United States Patent
Angerer et al.

(10) Patent No.: US 6,326,475 B1
(45) Date of Patent: Dec. 4, 2001

(54) DRY ACID-CHITOSAN COMPLEXES

(75) Inventors: J. David Angerer, Hockessin, DE (US); Donald M. Cyron, Lincoln University, PA (US); Subramanian Iyer, Hockessin, DE (US); Thomas A. Jerrell, Avondale, PA (US)

(73) Assignee: Arkion Life Sciences, Wilmington, DE (US)

( * ) Notice: Subject to any disclaimer, the term of this patent is extended or adjusted under 35 U.S.C. 154(b) by 0 days.

(21) Appl. No.: 09/515,051

(22) Filed: Feb. 25, 2000

Related U.S. Application Data

(60) Provisional application No. 60/121,391, filed on Feb. 25, 1999.

(51) Int. Cl.⁷ .......................... C08B 37/08; A61K 31/722
(52) U.S. Cl. ................. 536/20; 536/124; 514/55
(58) Field of Search ........................ 536/20, 124

(56) References Cited

U.S. PATENT DOCUMENTS

| | | | | |
|---|---|---|---|---|
| 4,574,150 | * | 3/1986 | Austin | 536/20 |
| 4,964,894 | * | 10/1990 | Freepons | 71/88 |
| 5,061,792 | * | 10/1991 | Albisetti et al. | 536/20 |
| 5,726,123 | * | 3/1998 | Heinsohn et al. | 504/140 |
| 6,130,321 | * | 10/2000 | Johnson et al. | 536/20 |
| 6,167,652 | * | 1/2001 | Heinsohn et al. | 47/58.1 |

FOREIGN PATENT DOCUMENTS

WO 96/41531 * 12/1996 (WO).

* cited by examiner

Primary Examiner—James O. Wilson
Assistant Examiner—Leigh C. Maier
(74) Attorney, Agent, or Firm—Basil S. Krikelis

(57) ABSTRACT

The invention is an acid-chitosan complex which is made up of chitosan, a sufficient amount of one or more acids, and an effective amount of water. This acid-chitosan is water-soluble in a dry form. A further aspect of this invention is various methods for producing such a water-soluble acid-chitosan complex and methods for using this acid-chitosan complex, particularly for reducing fat absorption in an animal.

2 Claims, No Drawings

DRY ACID-CHITOSAN COMPLEXES

RELATED APPLICATIONS

This application claims the benefit of U.S. Provisional Application No. 60/121,391, filed on Feb. 25, 1999.

FIELD OF THE INVENTION

The present invention relates to essentially dry complexes of acid and chitosan which are water-soluble. More specifically, the invention relates to water-soluble acid-chitosan complexes, methods for forming such complexes and uses of these acid-chitosan complexes for, among other things, prevention of fat digestion.

BACKGROUND OF THE INVENTION

When chitosan is prepared from the chitin fraction of the shells of crustacea, such as shrimp, crab and lobster, the final step is invariably and of necessity a treatment with extremely strong sodium hydroxide. This is the predominant industrial treatment that effectively removes acetyl groups from chitin, converting it into chitosan. Because of this treatment, chitosan is always found as an aminopolysaccharide with essentially none of the amino groups being protonated. This can be referred to as the free base form of chitosan. This natural form of chitosan is not soluble in water. In order to dissolve chitosan in water-based systems, the chitosan must be made more hydrophilic. This is done by adding acid to the water being used in dissolution. The acid reacts with the amino groups, converting them into (substituted) ammonium ions, which are much more hydrophilic than the amino groups. When chitosan is added to this acid-water mix, it becomes protonated. A fully protonated (i.e., each amino group has reacted with a proton from the acid) chitosan is the other extreme of chitosan. It should be noted, however, that essentially no protonation of chitosan will result if a dry acid and chitosan are merely physically blended. It is necessary to give the acid molecule mobility, which is done by the addition of water.

Chitosan is presently used as a dietary supplement to prevent some of the ingested fat in a person's diet from being absorbed and metabolized. It is thus an agent to help control obesity. When a person takes a dosage of chitosan, the chitosan exerts a demand on the stomach to produce hydrochloric acid in order to dissolve it. It is understood in the art that the chitosan must dissolve to be able to occlude the fat, which can thereafter be passed through the digestive tract and subsequently expelled from the body. Since the body's capacity for producing hydrochloric acid is limited, an agent that supplies part of the necessary acidity would be beneficial to chitosan's performance.

Merely treating chitosan with hydrochloric acid in a manufacturing process to form a water-soluble chitosan, however has an unintended and devastating side effect. It has been observed that these hydrochloric acid salts of chitosan undergo depolymerization upon storage, producing a product with too low a molecular weight to perform in the desired manner.

Presently, in the art, water-soluble chitosans are prepared by making a slurry of the chitosan in water and then adding acid to the slurry. Alternatively, one may make a solution of the acid and water and then add the chitosan under effective agitation conditions. It would be convenient, however, and represent an advance in the art, were all or part of the acid to be compounded with the chitosan thus providing a uniform dry complex which can be a shelf-stable product that will result in a reduced demand on the stomach for acid. To date, the only way to prepare such a complex has been achieved, with great difficulty, has been for the manufacturer to 1) dissolve the chitosan in aqueous acid, 2) filter the very viscous solution to remove insolubles, if necessary, and 3) spray dry the resulting solution to form a chitosan salt that is water soluble. Such a process is cumbersome, expensive and ineffective for an economically viable commercial process. Therefore, there is a need in the art for a more efficient and effective method of preparing chitosan salts.

SUMMARY OF THE INVENTION

It is a primary object of this invention to provide a water-soluble, acid-chitosan complex.

It is also an object of the invention to provide a water-soluble acid-chitosan complex produced by a process comprising:

(1) forming a homogenous mix of chitosan and a sufficient amount of an acid; and (2) adding an effective amount of water to the homogenous mix to form a uniform complex.

It is a further object of the invention to provide a water-soluble acid-chitosan complex produced by a process comprising:

(1) dissolving an acid in water; and (2) applying the acid-water mix to chitosan to form a complex wherein the chitosan is not dissolved; and (3) drying the complex.

It is an additional object of the invention to provide a method for reducing the release of triglycerides into the blood stream of an animal by administering to the animal an effective amount of a water-soluble acid-chitosan complex.

DETAILED DESCRIPTION OF THE INVENTION

The applicants have found that the physical blending of dry acid and chitosan, with the addition of controlled amounts of water, gives the acid molecules the needed mobility to accomplish protonation and thus move from a physical mixture to a complex (further defined below). The result of such a treatment is a state, or complex, somewhere between full-protonation and no protonation. The exact composition of the complex is dependent on the amount of water and acid used and the water solubility of the acid being used in the treatment. A more soluble acid, a higher amount of acid and/or the use of higher levels of water will result in a complex that is nearer to the fully-protonated extreme, whereas the use of a less soluble acid, lesser amounts of acid and/or lesser amounts of water will result in a complex that is much less protonated.

Definitions:

The following definitions apply throughout:

The term "acid-chitosan mixture" means the physical blend of dry acid and chitosan wherein no protonation of any significance of the chitosan occurs.

The term "acid-chitosan complex" means the mixture of acid and chitosan with the addition of controlled amounts of water to form a uniform, free-flowing mix such that the acid molecules attain the necessary mobility to accomplish at least partial protonation of the chitosan, to allow the acid-chitosan combination to become water-soluble.

The term "finished moisture level" means the weight percent of water in an acid-chitosan complex, based on the total weight of the complex, following the agitation step and before any optional or necessary drying of the complex is performed.

The Invention:

It is the applicants' discovery that a water-soluble acid-chitosan complex may be easily and effectively produced by adding varying amounts of one or more acids and a modest amount of water to a sufficiently-agitated chitosan powder or flake, mixing to achieve uniformity and, if necessary, drying the resulted hydrated crumb. By this technique, one can vary the amount of acid used from a very small amount up to essentially a stoichiometric quantity, and water-soluble acid-chitosan complexes may be prepared that range from completely water-soluble to hydratable and soluble by the addition of lesser quantities of acid than with native chitosan.

The technique and amount of water and acid addition are important to the successful practice of the present technology. Water is added as a carrier for the acid, allowing it to dissolve, ionize and penetrate the chitosan particle, and carry out at least partial protonation, thereby producing a complex of at least partial salt formation between the acid and the chitosan. If too little water is added, the acid molecules will not be sufficiently mobile to penetrate the particle and give a uniform product. If too much water is added, the hydrated chitosan will begin to approach a solution; this is not desired because large, hydrated gel masses may form and the product becomes very difficult to process through the necessary (in that case) drying and grinding operations required to produce a finished, marketable product. In this respect, it is preferred that the amount of water used be in the range of approximately 5% to 130% of the total weight of the chitosan and the acid, and more preferable that the amount of water added be in the range of 5% to 15%.

The acid to be used must be sufficiently water soluble to at least partially dissolve in the water used. In the case of less soluble acids, longer mix times may be necessary to give a more uniform product. This is generally necessary to form the water-soluble acid-chitosan complex, otherwise a true complex will not be formed, and instead, a partial complex and what is essentially a non-homogeneous mixture of acid and chitosan will form.

If the acid is a liquid, it is preferred that it be dissolved in the process water and thereafter sprayed onto the chitosan. If the acid is a solid, it may either be dry-blended or, if it is sufficiently water soluble, it may be dissolved in the water and the solution sprayed onto the chitosan powder or flake. Because a major necessity of the process is the diffusion of the acid, mediated by the water, into the chitosan solid, it may be easily seen that a period of mixing of the acid with the chitosan subsequent to the introduction of water to the chitosan is necessary to assure a homogeneous product.

The acids that are operative in the process preferably include, but are not limited to, hydrochloric, acetic, lactic, glycolic, nitric, malic, pyruvic, citric, ascorbic, and other physiologically acceptable carboxylic acids. Other acidic substances, such as betaine hydrochloride or amine hydrochlorides, such as glycine hydrochloride, which are more acidic than the amino group on chitosan, are also effective.

The crux of the invention is that the use of acid and water with the chitosan and with good agitation allows a reaction between the acid and the chitosan, resulting in the formation of a true chemical complex, rather than just an intimate blend of the two components. The complex can be best described as a salt of chitosan, acting as a base, with one or more acidic species(see definition above).

It is applicants' discovery that mixtures of acids with chitosan, in amounts that approach or exceed stoichiometric for salt formation, provide superior performance in the fat-binding application. In a particular embodiment, acceptable betaine hydrochloride complexes with chitosan surprisingly show efficacy in the application and demonstrate good shelf stability, making them especially suitable for the application.

Further, the applicants have found a method of preparing these chitosan salts which results in at least partial salt formation, taking the formulation from a mixture of chitosan and acid to the formation of an acid-chitosan complex. This provides for a uniform product which may be easily formulated into the final marketable product, but is still stable with regard to molecular weight of the chitosan over time.

A preferred embodiment is the complex of chitosan with betaine hydrochloride. The applicants have found that a dry blend of 100 parts of chitosan and 75 parts of betaine hydrochloride, when treated with water according to the invention to form a complex, forms a homogeneous, water soluble solid. Conversely, when a dry blend or mixture was prepared of the two compounds in the same ratio, the two materials separated, due to their large difference in bulk density, and samples taken from different parts of the container showed greatly different solubility properties.

The preparation of the betaine hydrochloride complex of chitosan also demonstrates the criticality of the use of controlled amounts of water. In this case, when 100 parts of chitosan were treated with 75 parts of betaine hydrochloride and 200 parts of water (which is equivalent to 115% of the total weight of the chitosan and the acid), a granular hydrated chitosan/betaine hydrochloride complex was formed, which was easily dried and ground to give product. However, when the water was increased to 250 parts (equivalent to 143% of the chitosan and the acid), the material became sufficiently hydrated and cohesive to form a stiff, gel-like mass which actually froze the blades of the Hobart mixer, causing the motor to burn out. Drying this gummy mass was quite difficult, as the gel held water for long periods of time. Upon reaching a dry state, the product formed large, extremely hard pieces of the salt, making it very difficult to grind.

In one particular embodiment, wherein the amount of acid is sufficient to protonate enough of the amino groups of chitosan to yield a soluble product (i.e. 75% of stoichiometric or higher), the applicants have found that adding 10% water, based on the sum of the weights of chitosan and betaine hydrochloride, to a mixture of chitosan and betaine hydrochloride and mixing after the addition, gives a dry powder which easily disperses and dissolves in water to give a viscous chitosan solution.

In an alternative embodiment, applicants have treated the chitosan in the manner of the invention with lesser amounts of acid to give products that disperse in water and, upon the addition of lesser than usually employed amounts of acid, form a viscous solution of chitosan.

Low levels of acid generally yield chitosan complexes that are not soluble in water (i.e. not enough of the salt has been formed to render the chitosan water- soluble in its own right). This reinforces the fact that there must be an adequate number of moles of acid present to protonate a major fraction of the amine groups in the chitosan. For example, full solubilization requires at least about 0.75 moles of acid for each mole of chitosan. The acid content to be achieved will depend on how much one wants to decrease the acid demand on the stomach of an ingester of the complex.

Another aspect of the invention relates to the use of water-soluble acid-chitosan complexes in the prevention of fat digestion and the overall improvement of an animal's health. In particular it is applicants' discovery that when an effective amount of a water-soluble acid-chitosan complex, and in particular, that of chitosan and betaine hydrochloride, is administered to an animal prior to or during digestion of fat-containing substances, the triglyceride levels within that animal are reduced to levels significantly below those observed with the use of chitosan as known in the prior art. Triglyceride levels are known in the art as a measure of fat availability within an animal's system. The following paragraph sets forth a description of trigycerides.

A triglyceride is a primary form of fat transported within an animal's body. Triglycerides are found as a normal component in an animal's bloodstream. They are compounds (esters) of fatty acids and glycerol that bind to proteins and form low-density lipoprotein (LDL) and verylow density lipoprotein (VLDL). Normally, triglyceride levels rise immediately after eating. In particular, after an animal eats, its body digests the fats from the food and then releases triglycerides into the bloodstream. The triglycerides are transported throughout the body of the animal to give the animal energy or they are easily stored as fat. Thus, as is known in the prior art, a reduction in the level of triglycerides is directly correlated to a reduction in the fat available to the body through the digestive process.

The liver also produces triglycerides and converts some into cholesterol. Further, there is a link between triglyceride levels and the development of coronary heart disease. High triglyceride levels are an important predictor of myocardial infarction. LDL and VLDL contain large amounts of cholesterol and triglycerides that can adhere to the arteries in the form of fatty plaques. Therefore, a reduction in triglycerides has several beneficial aspects.

The administration of the acid-chitosan complex to an animal also has a beneficial effect on the levels of aspartate aminotransferase (AST) and alanine aminotransferase (ALT) in that animal. The levels of AST and/or ALT in an animal relate to characteristics of liver function. For example, ALT levels are present in kidney and muscle as well as liver, and are used to confirm that AST elevations are of liver origin.

It is Applicants' discovery that with the administration of a water-soluble acid-chitosan complex, and particularly chitosan and betaine hydrochloride, the ALT and AST levels were generally found to be significantly lower than that in commercially available chitosan and even the positive control of the drug Xenical™. Water-soluble acid-chitosan complexes are found to be less hepatotoxic than commercially available Chitosan or Xenical™ in animals being fed such products.

The advantageous properties of this invention can be further observed by reference to the following examples which illustrate the invention.

EXAMPLES

Example 1

Sixty five grams of ground chitosan (−60 mesh), available from DCV, Inc., Wilmington, Del., was added to a Hobart mixer. Hydrochloric acid (6.5 g on a 100% acid basis) was added to enough water to make 150 ml total solution. The mixer was started at medium speed and the acid solution was sprayed onto the mix over a 5-minute period. Mixing was continued for 15 minutes following the addition of acid to yield a homogeneous, moist crumb. At that point, the moist acid-chitosan complex was put into an aluminum tray and dried overnight in a convection oven, set at 65° C. When dry, the material was re-ground to −60 mesh. The grinder used was a Tekmar grinder with cooling jacket, Model No. A-10.

To test water solubility, a 1.5 g portion was put into a beaker with 150 g of water. A magnetic stirring bar was placed in the beaker and the solution was mixed for one hour. The solid dissolved to give a viscous solution.

Example 2

Sixty-five (65) grams of chitosan flake was added to a Waring blender. Solid betaine hydrochloride (48 g) was added to the chitosan. The mixer was started at low speed and 100 ml of water was sprayed on over a 5-minute period. Following the addition of water, the blend was mixed for an additional 10 minutes to form the homogeneous acid-chitosan complex. The moist complex was dried overnight at 55° C. and was then ground to −20 mesh using the Tekmar grinder. 2 g of this was added to water and stirred to give a viscous solution.

Example 3

Seventy five (75) pounds of chitosan was added to a Henschel mixer. Solid betaine hydrochloride (56 lbs.) was added to the chitosan. The mixer was started at low speed and 10 lbs. Of water was sprayed on over a 2 minute period. Following the addition of water, the blend was mixed for 15 minutes to form the homogenous acid-chitosan complex, which was then screened through a 20 mesh screen and packaged. Two grams of this was added to 100 ml of water. A gel was formed within 1 minute with a pH of approximately 3 with no additional acid added.

Example 4

A sample of untreated chitosan (2 g at 6.7% moisture= 1.87 g chitosan on a 100% basis) was placed in 200 ml of water. The initial pH of the slurry was 7.3. One normal (1N) hydrochloric acid was added dropwise, with stirring, until a solution was formed and the final pH was 3.0. It was found that 7.75 ml of acid were required, or 4.144 meq/gm of 100% chitosan.

In a like manner, chitosan from the same original lot that had been treated in the manner of the invention such as to form the acid-chitosan complex with a 10% ratio of 100% hydrochloric acid to chitosan (2 g at 1.4 % moisture, representing 1.79 g of 100% chitosan) was dissolved and adjusted to pH 3.0. While the pH of the water before introduction of the chitosan was observed to be 7.30, the pH drifted down to 5.7 before any acid was added and the chitosan was observed to visibly begin to hydrate, indicating partial solubility ascribed to partial formation of the acid-chitosan complex. It was found that the treated sample required only 5.4 ml of acid (corresponding to 3.016 meq/gm of 100% chitosan) to lower the pH to 3.0. This is direct confirmation that partial complex formation had occurred and that there was a reduced acid demand to effect solution.

Example 5

The purpose of this study was to (1) to compare the fat binding ability of Betasanne™ (chitosan and betaine hydrochloride complex prepared by any of the methods described in the above examples) with that of various commercially available chitosans; (2) to optimize the conditions for maximum absorption of fat from the diet using Betasanne™ or commercially available chitosan; and (3) to compare the efficacy of fat binding using Betasanne with that of commercially available chitosan.

Study Design

TABLE 1

| Group | Number of Animals | Test Article |
|---|---|---|
| 1 | 12 | Mixture of Chitosan and 5% Vitamin C |
| 2 | 12 | Chitosan |
| 3 | 12 | Chitin |
| 4 | 12 | Betasanne ™ |
| 5 | 12 | Mixture of Chitosan and 1% Vitamin C |
| 6 | 12 | High Fat Diet |
| 7 | 12 | Xenical ™ |
| 8 | 12 | Low Fat Diet |

All rats were fed a basal diet for 5 days prior to initiation of dosing on Day 0. At Day 0, animals in Groups 1 to 5 and 7 received the appropriate formulated diet. The diet was available ad libitum. Animals in Group 6 received only the basal diet throughout the study and animals in Group 8 received Purina Diet #5001 without the addition of additional fat throughout the study. The total amount of the diet consumed by each animal was determined every 3 to 4 days.

Results

Table 2 below outlines differences in weight gain and triglyceride, AST and ALT levels in the blood of the rats used in the trial as sert forth above.

TABLE 2

|  | Chitosan + 5% Vit C | Betasanne | Chitosan | Chitosan + 1% Vit C | Xenical | High Fat | Low Fat |
|---|---|---|---|---|---|---|---|
| Weight Gain (gms) | 419 | 444 | 464 | 458 | 425 | 469 | 452 |
| Triglycerides (mg/dL) | 133 | 119 | 157 | 141 | 107 | 172 | 111 |
| ALT (IU/L) | 52 | 46 | 54 | 48 | 54 | 41 | 38 |
| AST (IU/L) | 80 | 63 | 73 | 64 | 104 | 67 | 83 |
| Bilirubin (mg/dL) | 0.4 | 0.3 | 0.5 | 0.5 | 0.4 | 0.6 | 0.2 |

Note: For all number values in Table 2, the lower the number, the more effective the product)

Conclusion and Summary

On the basis of equal weighting for all the properties that were measured in this study, the two groups which used an acid-chitosan complex as set forth in the invention showed the greatest effects (i.e. Betasanne and Chitosan+5% ascorbic acid). The animals administered Betasanne or Chitsan+5% ascorbic gained less weight than did those animals administered either commercially available chitosan or a high fat diet. Similar results were observed for triglyceride levels.

As for ALT and bilirubin levels, Betasanne is the closest to the high fat and low fat diet, thus showing that it is the least hepatotoxic.

We claim:

1. An acid-chitosan complex comprising chitosan, about 0.75 molecules or more of betaine hydrochloride per amino group of chitosan, and an effective amount of water, said amount of water being about 5% to 130% of the combined weight of the betaine hydrochloride and the chitosan, on a weight to weight basis, wherein said acid-chitosan complex is water-soluble.

2. The acid-chitosan complex of claim 1 wherein the effective amount of water comprises about 5% to 15% of the combined weight of the betaine hydrochloride and the chitosan on a weight to weight basis.

* * * * *